United States Patent
Yudina

(10) Patent No.: US 12,152,058 B2
(45) Date of Patent: Nov. 26, 2024

(54) APPARATUS AND METHOD FOR OBTAINING PROTEIN-ENRICHED FRACTIONS FROM BREAST MILK

(71) Applicant: BABYLAT AG, Bern (CH)

(72) Inventor: Zinaida Yudina, Wohlen AG (CH)

(73) Assignee: BABYLAT AG, Bern (CH)

( * ) Notice: Subject to any disclaimer, the term of this patent is extended or adjusted under 35 U.S.C. 154(b) by 0 days.

(21) Appl. No.: 18/181,939

(22) Filed: Mar. 10, 2023

(65) Prior Publication Data

US 2023/0220023 A1    Jul. 13, 2023

Related U.S. Application Data

(63) Continuation of application No. PCT/EP2021/050366, filed on Jan. 11, 2021.

(51) Int. Cl.
*C07K 1/34* (2006.01)
*A23C 9/142* (2006.01)
(Continued)

(52) U.S. Cl.
CPC ............ *C07K 14/47* (2013.01); *A23C 9/1422* (2013.01); *A23C 9/206* (2013.01); *B01D 61/027* (2013.01);
(Continued)

(58) Field of Classification Search
CPC ........ C07K 14/47; C07K 1/34; A23C 9/1422; A23C 9/206; A23C 3/03; B01D 61/027; B01D 61/04; B01D 61/08; B01D 61/147; B01D 61/18; B01D 61/58; B01D 69/02; B01D 71/04; B01D 2311/04; B01D 2311/06; B01D 2313/243; B01D 2313/32; B01D 2317/025; B01D 2325/02834; B01D 2325/20; B01D 61/146; B01D 2317/08;
(Continued)

(56) References Cited

U.S. PATENT DOCUMENTS 3,911,108 A   10/1975   Singh
4,051,235 A    9/1977   Plymate
(Continued)

FOREIGN PATENT DOCUMENTS

BG         105016 U      3/2003
CA        2360837 A1     8/2000
(Continued)

OTHER PUBLICATIONS

Andreas et al., (2015). "Human Breast Milk: A review of its composition and bioactivity," Early Human Development, 91(11):629-635, 19 pages.
(Continued)

*Primary Examiner* — Helena Kosanovic
*Assistant Examiner* — Tiffany T Tran
(74) *Attorney, Agent, or Firm* — Morrison & Foerster LLP

(57) ABSTRACT

A device for obtaining protein-enriched fractions from human or animal milk comprises a delipidating unit for reducing a lipid content in the human or animal milk to obtain delipidated milk and a filtering unit for increasing a protein concentration of the delipidated milk to obtain the protein-enriched fraction, comprising a replaceable filter having a nominal molecular weight limit of 2 kDa or more, in particular of 5 kDa or more.

11 Claims, 2 Drawing Sheets

(51) Int. Cl.

| | |
|---|---|
| *A23C 9/20* | (2006.01) |
| *B01D 61/02* | (2006.01) |
| *B01D 61/04* | (2006.01) |
| *B01D 61/08* | (2006.01) |
| *B01D 61/14* | (2006.01) |
| *B01D 61/18* | (2006.01) |
| *B01D 61/58* | (2006.01) |
| *B01D 69/02* | (2006.01) |
| *B01D 71/04* | (2006.01) |
| *C07K 14/47* | (2006.01) |

(52) U.S. Cl.
CPC ............ *B01D 61/04* (2013.01); *B01D 61/08* (2013.01); *B01D 61/147* (2013.01); *B01D 61/18* (2013.01); *B01D 61/58* (2013.01); *B01D 69/02* (2013.01); *B01D 71/04* (2013.01); *C07K 1/34* (2013.01); *B01D 2311/04* (2013.01); *B01D 2311/06* (2013.01); *B01D 2313/243* (2013.01); *B01D 2313/32* (2013.01); *B01D 2317/025* (2013.01); *B01D 2325/02834* (2022.08); *B01D 2325/20* (2013.01)

(58) Field of Classification Search
CPC .......... B01D 2311/2649; B01D 61/145; B01D 61/16; B01D 65/08; B01D 63/087; B01D 2315/08; A23L 33/40
See application file for complete search history.

(56) References Cited

U.S. PATENT DOCUMENTS

| | | | |
|---|---|---|---|
| 4,644,056 A | 2/1987 | Kothe et al. | |
| 4,784,850 A | 11/1988 | Abraham | |
| 5,147,548 A | 9/1992 | Hies et al. | |
| 6,096,870 A | 8/2000 | Mozaffar et al. | |
| 6,162,472 A | 12/2000 | Griffin et al. | |
| 6,444,247 B1 | 9/2002 | Gorewit | |
| 8,826,810 B1* | 9/2014 | Norelius | A01J 11/16 99/452 |
| 9,776,138 B2 | 10/2017 | Innings et al. | |
| 2003/0059512 A1* | 3/2003 | Kopf | A23C 9/1425 426/582 |
| 2004/0028667 A1 | 2/2004 | Norman et al. | |
| 2004/0219266 A1 | 11/2004 | Milliken et al. | |
| 2006/0102016 A1 | 5/2006 | Ulrich et al. | |
| 2006/0204632 A1 | 9/2006 | Barrett-Reis et al. | |
| 2006/0210668 A1* | 9/2006 | Thorsoe | A23C 9/1542 426/42 |
| 2007/0166447 A1 | 7/2007 | Ur-Rehman et al. | |
| 2008/0050498 A1* | 2/2008 | Sherwood | A23L 2/39 426/594 |
| 2008/0075819 A1 | 3/2008 | Hartmann et al. | |
| 2009/0028990 A1 | 1/2009 | Kwon et al. | |
| 2010/0112152 A1* | 5/2010 | Sinnema | A23L 33/40 99/287 |
| 2010/0221359 A1 | 9/2010 | Gohlke et al. | |
| 2011/0206684 A1 | 8/2011 | Medo | |
| 2013/0059050 A1* | 3/2013 | Fournell | A23C 9/1422 426/491 |
| 2014/0193555 A1 | 7/2014 | Czank et al. | |
| 2014/0271980 A1 | 9/2014 | Eaker et al. | |
| 2014/0272027 A1 | 9/2014 | Elster et al. | |
| 2014/0302219 A1* | 10/2014 | Tikanmaki | A23C 9/1425 426/491 |
| 2015/0099036 A1* | 4/2015 | Aichinger | A23C 9/137 426/71 |
| 2015/0305383 A1 | 10/2015 | Georgi et al. | |
| 2016/0021904 A1 | 1/2016 | Verdi | |
| 2016/0362477 A1 | 12/2016 | Sand et al. | |
| 2017/0164630 A1 | 6/2017 | Dimauro et al. | |
| 2017/0172167 A1 | 6/2017 | Silver et al. | |
| 2017/0196234 A1 | 7/2017 | Puigferrat et al. | |
| 2017/0280737 A1* | 10/2017 | Liao | C02F 1/325 |
| 2018/0343880 A1* | 12/2018 | Metzger | A23C 9/1524 |
| 2019/0223461 A1 | 7/2019 | Ur-Rehman et al. | |
| 2019/0263583 A1 | 8/2019 | Downie et al. | |
| 2019/0376942 A1 | 12/2019 | Birlouez-Aragon | |
| 2020/0196620 A1 | 6/2020 | Arena et al. | |
| 2020/0359642 A1* | 11/2020 | Fournell | A23C 9/206 |
| 2021/0239671 A1 | 8/2021 | Suhr et al. | |
| 2024/0009244 A1 | 1/2024 | Yudina et al. | |

FOREIGN PATENT DOCUMENTS

| | | |
|---|---|---|
| CN | 1037276 A | 11/1989 |
| CN | 101014253 A | 8/2007 |
| CN | 101605470 A | 12/2009 |
| CN | 101731446 A | 6/2010 |
| CN | 102630803 A | 8/2012 |
| CN | 204466781 U | 7/2015 |
| CN | 106417888 A | 2/2017 |
| CN | 107576625 A | 1/2018 |
| CN | 109122855 A | 1/2019 |
| CN | 109452178 A2 | 3/2019 |
| CN | 110214703 A | 9/2019 |
| CN | 209628538 U | 11/2019 |
| CN | 113457452 A | 1/2021 |
| CN | 112642294 A | 4/2021 |
| CN | 112913871 A | 6/2021 |
| CN | 113287656 A | 8/2021 |
| DE | 283937 A5 | 4/1989 |
| DE | 4118168 A1 | 1/1993 |
| DE | 9117058 U1 | 6/1995 |
| DE | 19510969 A1 | 9/1996 |
| DE | 19548221 C1 | 5/1997 |
| DE | 102006053017 A1 | 5/2008 |
| DE | 102013219932 A1 | 4/2015 |
| DE | 102021105641 A1 | 9/2022 |
| EP | 0173999 A2 | 3/1986 |
| EP | 0316938 A2 | 5/1989 |
| EP | 0338229 A1 | 10/1989 |
| EP | 0391416 A1 | 10/1990 |
| EP | 0398802 A1 | 11/1990 |
| EP | 0410272 A1 | 1/1991 |
| EP | 0363896 A2 | 8/1994 |
| EP | 0638242 A2 | 2/1995 |
| EP | 0741976 A1 | 11/1996 |
| EP | 1055372 A2 | 11/2000 |
| EP | 1637880 A1 | 3/2006 |
| EP | 1982599 A1 | 10/2008 |
| EP | 2280999 A1 | 2/2011 |
| EP | 2572593 A1 | 3/2013 |
| EP | 2762490 A1 | 8/2014 |
| EP | 2833767 A1 | 2/2015 |
| EP | 2675281 B1 | 4/2015 |
| EP | 2896294 A1 | 7/2015 |
| EP | 2926843 A1 | 10/2015 |
| EP | 2992900 A1 | 3/2016 |
| EP | 3056276 A2 | 8/2016 |
| EP | 3225114 A1 | 10/2017 |
| EP | 3281683 A1 | 2/2018 |
| EP | 3298903 A1 | 3/2018 |
| EP | 2914612 B1 | 11/2018 |
| EP | 3476220 A1 | 5/2019 |
| EP | 3496544 A1 | 6/2019 |
| EP | 2334190 B1 | 9/2020 |
| EP | 3175238 B1 | 8/2021 |
| EP | 3855897 A1 | 8/2021 |
| EP | 3949741 A1 | 2/2022 |
| EP | 4063834 A1 | 9/2022 |
| GB | 2273885 A | 7/1994 |
| GB | 2525921 A | 11/2015 |
| GB | 2544100 A | 5/2017 |
| NZ | 511562 A | 10/2003 |
| PT | 90318 A | 11/1989 |
| WO | WO-1989011226 A1 | 11/1989 |
| WO | WO-1995010192 A1 | 4/1995 |
| WO | WO-1996032021 A1 | 10/1996 |
| WO | WO-1999015024 A1 | 4/1999 |
| WO | WO-2000060949 A2 | 10/2000 |

(56) References Cited

FOREIGN PATENT DOCUMENTS

| | | |
|---|---|---|
| WO | WO-2001003515 A1 | 1/2001 |
| WO | WO-2003100377 A2 | 12/2003 |
| WO | WO-2006026879 A1 | 3/2006 |
| WO | WO-2006119560 A1 | 11/2006 |
| WO | WO-2007035870 A2 | 3/2007 |
| WO | WO-2008027572 A1 | 3/2008 |
| WO | WO-2008067486 A2 | 6/2008 |
| WO | WO-2008073888 A2 | 6/2008 |
| WO | WO-2008127104 A1 | 10/2008 |
| WO | WO-2008144922 A1 | 12/2008 |
| WO | WO-2008146276 A1 | 12/2008 |
| WO | WO-2009092629 A1 | 7/2009 |
| WO | WO-2009139624 A1 | 11/2009 |
| WO | WO-2010065652 A1 | 6/2010 |
| WO | WO-2010128051 A1 | 11/2010 |
| WO | WO-2012030764 A2 | 3/2012 |
| WO | WO-2012110705 A1 | 8/2012 |
| WO | WO-2013020081 A2 | 2/2013 |
| WO | WO-2013068653 A2 | 5/2013 |
| WO | WO-2013137714 A1 | 9/2013 |
| WO | WO-2013150070 A1 | 10/2013 |
| WO | WO-2014125382 A1 | 8/2014 |
| WO | WO-2014163486 A1 | 10/2014 |
| WO | WO-2015056166 A1 | 4/2015 |
| WO | WO-2015103561 A1 | 7/2015 |
| WO | WO-2015128512 A1 | 9/2015 |
| WO | WO-2015168418 A1 | 11/2015 |
| WO | WO-2016022152 A1 | 2/2016 |
| WO | WO-2016109659 A1 | 7/2016 |
| WO | WO-2016168167 A1 | 10/2016 |
| WO | WO-2016168698 A1 | 10/2016 |
| WO | WO-2017027081 A1 | 2/2017 |
| WO | WO-2017048881 A1 | 3/2017 |
| WO | WO-2017090049 A1 | 6/2017 |
| WO | WO-2017117409 A1 | 7/2017 |
| WO | WO-2017220697 A1 | 12/2017 |
| WO | WO-2018028764 A1 | 2/2018 |
| WO | WO-2018028765 A1 | 2/2018 |
| WO | WO-2018029222 A1 | 2/2018 |
| WO | WO-2018053535 A1 | 3/2018 |
| WO | WO-2018122695 A1 | 7/2018 |
| WO | WO-2018132676 A1 | 7/2018 |
| WO | WO-2018202636 A1 | 11/2018 |
| WO | WO-2019126308 A1 | 6/2019 |
| WO | WO-2019160402 A1 | 8/2019 |
| WO | WO-2019160416 A1 | 8/2019 |
| WO | WO-2020002422 A1 | 1/2020 |
| WO | WO-2020067883 A1 | 4/2020 |
| WO | WO-2020115196 A1 | 6/2020 |
| WO | WO-2020140185 A1 | 7/2020 |
| WO | WO-2020168439 A1 | 8/2020 |
| WO | WO-2020176607 A1 | 9/2020 |
| WO | WO-2020212954 A1 | 10/2020 |
| WO | WO-2022081623 A1 | 4/2022 |
| WO | WO-2022085007 A1 | 4/2022 |
| WO | WO-2022148549 A1 | 7/2022 |
| WO | WO-2022159989 A1 | 7/2022 |
| WO | WO-2022182837 A1 | 9/2022 |

OTHER PUBLICATIONS

Bertino et al., (2017). "New human milk fortifiers for the preterm infant," Journal of Pediatric and Neonatal Individualized Medicine, 6(1):e060124, 7 pages.

Colaizy et al., (2016). "Impact of Optimized Breast Feeding on the Cost of Necrotizing Enterocolitis in Extremely Low Birthweight Infants," J. Pediatr., 175:100-105.e2, 16 pages.

Embleton et al., (2013). "Effectiveness of Human Milk-Based Fortifiers for Preventing Necrotizing Enterocolitis in Preterm Infants: Case Not Proven," Breastfeed. Med., 8(4):421.

International Search Report and Written Opinion received for International Patent Application No. PCT/EP2021/050366 mailed on May 7, 2021. 7 pages.

Lonnerdal et al., (2017). "Longitudinal evolution of true protein, amino acids and bioactive proteins in breast milk: a developmental perspective," Journal of Nutritional Biochemistry, 41:1-11.

Martin et al., (2016). "Review of infant feeding: Key features of breast milk and infant formula," Nutrients, 8(5):279, 11 pages.

Moro et al., (2015). "Human Milk in Feeding Premature Infants: Consensus Statement," JPGN, 61(1):S16-S19.

Van't Land et al., (2010). "Chapter 2: Breast Milk: Components with Immune Modulating Potential and Their Possible Role in Immune Mediated Disease Resistance," Dietary Components and Immune Function, 25-41.

Victora et al., (2016). "Breast feeding in the 21st century: Epidemiology, mechanisms, and lifelong effect," Lancet, 387(10017):475-490, 16 pages.

Extended European Search Report and Opinion received for European Patent Application No. 23184820.1 mailed on Nov. 22, 2023, 9 pages.

* cited by examiner

APPARATUS AND METHOD FOR OBTAINING PROTEIN-ENRICHED FRACTIONS FROM BREAST MILK

CROSS-REFERENCE TO RELATED APPLICATION

This application is a continuation of International Application No. PCT/EP2021/050366, filed internationally on Jan. 11, 2021, the disclosure of which is incorporated by reference in its entirety for all purposes.

TECHNICAL FIELD

The present invention relates to a device and a method for obtaining protein-enriched fractions from human or animal milk as well as to a protein-enriched fraction of milk obtained from the method and to a use thereof.

BACKGROUND ART

Breastfeeding with breast milk is commonly regarded as very important for the development of newborns. Breastmilk is uniquely adapted to the needs of human babies, providing them with the nutrients they need to grow and thrive, but at the same time incorporating a multitude of immunological, antibacterial and in general antipatogenic factors and epigenetic effects that the industry needs can not be reproduced. Bioactive proteins can have enzymatic activity, enhance nutrient absorption, stimulate growth, modulate the immune system and assist in the defense against pathogens. Key bioactive proteins in human milk include lysozyme, α-lactalbumin, κ-casein and β-casein, as well as lactoferrin and immunoglobulins, especially sIgA [1] (REF: [1] B. Löhnerdal, P. Erdmann, S. K. Thakkar, J. Sauser, and F. Destaillats, "Longitudinal evolution of true protein, amino acids and bioactive proteins in breast milk: a developmental perspective," Journal of Nutritional Biochemistry. 2017 and [2] C. R. Martin, P. R. Ling, and G. L. Blackburn, "Review of infant feeding: Key features of breast milk and infant formula," Nutrients. 2016.)

Breast milk is the only known substance that has nourishing and at the same time immune-modulating functions for the child organism. The composition of breast milk changes over time. And there are suggestions that at the end of first year and after the nourishing function of breastfeeding in newborns decreases at the age of one year and above, and the immune-modulating function increases [REF: B. VAN'T LAND, G. BOEHM, J. GARSSEN: Breast Milk: Components with Immune Modulating Potential and Their Possible Role in Immune Mediated Disease Resistance, in: Dietary Components and Immune Function, 2010; M. T. PERRIN, A. FOGLEMAN, J. C. ALLEN: The nutritive and immunoprotective quality of human milk beyond 1 year postpartum: are lactation-duration-based donor exclusions justified? In Journal of Human Lactation. 2013].

Still, breastfeeding rates are generally too low, especially in developed countries. Due to socio-economic conditions, and especially because of their professional activity, women often do not have enough time to fulfill the ideal breastfeeding criteria (continuous breastfeeding, ie breastmilk with solid food) for up to two years and beyond. In developed countries, only 25% of mothers quit after 10 months or more [REF: C. G. VICTORA ET AL.: Breast feeding in the 21st century: Epidemiology, mechanisms, and lifelong effect, in The Lancet, vol. 387, no. 10017. pp. 475-490].

In order to close the gap between the actual breastfeeding rate and the physiological needs of babies infant formula milk products are available, mainly based on cow's milk. However, these products are inferior to breast milk in their physiological effects. In particular, they absolutely can not fulfill the immunomodulatory functions of breast milk [REF: N. J. ANDREAS, B. KAMPMANN, K. MEHRING LE-DOARE: Human Breast Milk: A review of its composition and bioactivity, in Early Human Development, vol. 91, no. 11. pp. 629-635, 2015; J. PENDERS: Early diet and the infant good microbiome How breastfeeding and solid foods shape the microbiome, in Microbiota in health and disease: from pregnancy to childhood, 2017].

A particular problem is revealed in premature infants. Also, they ideally need breast milk (from their mother or a donor). However, the composition of human milk is not geared to the needs of premature babies. Premature babies need a higher protein content. As a result of protein deficiency, there is a risk that premature babies are disturbed in their growth. To counteract this problem, cow's milk, donkey's milk or soy proteins are added to the donor milk in order to increase their nutritional value (so-called enrichment process). However, enrichment with proteins of non-human origin leads to risks, in particular for gastrointestinal diseases, increased risks of infection increased risk of allergies and increase the risk of NEC—the leading mortality cause of preterm babies [REF: T. T. Colaizy et al.: Impact of Optimized Breast Feeding on the Cost of Necrotizing Enterocolitis in Extremely Low Birthweight Infants, in J. Pediatr., 2016; N. D. Embleton et al.: Effectiveness of Human Milk-Based Fortifiers for Preventing Necrotizing Enterocolitis in Preterm Infants: Case Not Proven, Breastfeed. Med., 2013].

Processes for obtaining protein-enriched fractions from breast milk are known and have been described, inter alia in EP 0 173 999 A2 (Biotest Pharma GmbH). The pH of the milk is reduced and the milk is filtered using a cross-flow filtration unit. Low-molecular weight components are removed from the resulting filtrate by a second cross-flow filtration.

Isolation and/or enrichment of protein-rich fractions from milk is now commonly done by means of laboratory methods by appropriately trained professionals.

SUMMARY OF THE INVENTION

It is the object of the invention to create a device for obtaining protein-enriched fractions from human or animal milk pertaining to the technical field initially mentioned, that simplifies the process, especially for on-site application.

The solution of the invention is specified by the features of claim 1. According to the invention the device comprises
a) a delipidating unit for reducing a lipid content in the human or animal milk to obtain delipidated milk; and
b) a filtering unit for increasing a protein concentration of the delipidated milk to obtain the protein-enriched fraction, comprising a replaceable filter having a nominal molecular weight limit (NMWL) of 2 kDa or more, in particular of 5 kDa or more.

In the filtering unit, an ultrafiltration step takes place. In particular, the corresponding filter has a membrane pore size which is at least two times less than the weight of the target molecules in the permeate. The pore size can be varied so that the filtrate has the desired proteins. Usually, the NMWL it should not exceed 10 kDa.

Preferably, the delipidating unit and the filtering unit are integrated as components of the device. However, these units can also be configured as separate modules or modules that can be combined to form a structural unit. The device is a functional unit that allows the recovery of protein-enriched fractions from the human or animal breast milk outside the laboratory. The device may be designed in such a way that its use does not require any professional laboratory knowledge, but may also be used by laymen (especially mothers and nurses).

According to the invention, a method for obtaining protein-enriched fractions from human or animal milk, comprises the steps of:
  a) reducing a lipid content in the human or animal milk to obtain delipidated milk; and
  b) increasing a protein concentration of the delipidated milk to obtain the protein-enriched fraction by filtering the delipidated milk using a filter having a nominal molecular weight limit of 2 kDa or more, in particular of 5 kDa or more.

In particular, the pH of the milk is not modified, but the product is obtained substantially be reducing the lipid content and subsequent filtering.

Reducing the lipid content avoids fouling of the nanofilter for the increase of protein concentration.

The present invention provides an easy-to-use device or an easily performed method which allows the isolation of protein-enriched fractions of breast milk even by persons without laboratory technical knowledge, in particular also by mothers and nurses. In particular, the present invention gives mothers the opportunity to stock up on their newborn important fractions of breast milk to continue to provide for the infant even after breastfeeding has stopped. However, the present invention also makes it possible, with a view to the optimal nutrition of preterm infants, to condition breast milk in its ingredients (in particular with regard to protein content). Also conceivable are other applications of the present invention, in particular in the field of recovery of breast milk or of fractions thereof by nurses.

The suggested device allows for substantially reducing the final cost of human milk origin fortifiers (HMOF) compared with current industrial products.

It makes them more available in developed countries and especially in developing ones, providing better outcome for preterm infants. HMOF wide administration would reduce also the total duration of hospitalization of the infants, meaning less spending for hospitals.

If hospitals prepare the protein fortifier from the milk, collected locally, it reduces also the cost of the donor milk itself and thus can decrease further the price of HMOF prepared using the inventive device and method on site. Furthermore, the impact on the environment may be reduced because the product does not have to be shipped, it is prepared on site for local consumption.

Depending on the indication, the filtrate of the filtered permeate is suitable for direct administration to the premature or newborn or for preservation in stock. The present invention may also be applied to the rearing of animals, including within the framework of zoological breeding programs.

Due to the simple device and method, the risk of losing proteins is substantially reduced compared to long elaborative protocols with multiple steps. Accordingly, the protein yield after enrichment may be increased.

Preferably, the delipidating unit comprises a replaceable filter. In the corresponding delipidating unit, the filtrated, delipidated milk (filtrate) with the immunoglobulins, alpha-lactalbumin, serum albumin, lactoferrin and the other components (lactose, minerals, micronutrients etc.) is obtained as permeate.

In today's large scale processes, delipidation is usually based on centrifugation because it was assumed that filters would be immediately blocked by the lipids. Surprisingly, it has been found that the composition of human milk lipid micelles allows to have an efficient filtering process—compared to e. g. cow micelles. It is not even mandatory to employ a cross-flow filtering process, but dead-end filtration is also applicable. This simplifies the process and the buildup of a corresponding device.

In a preferred embodiment, the filter of the delipidating device is a glass microfiber filter. It has been found that the micelles, in particular of human milk, stay inside of a multilayer glass microfiber filter.

The filter material may be different, but should be particularly suitable for labile proteins to achieve minimal absorption and protein loss and same time allow to not penetrate the lipid fraction inside the filtrate.

Preferably, the filter of the delipidating device has a pore size of less than 0.5 µm, preferably of less than 0.35 µm. Correspondingly, the lipid content is reduced by microfiltration, employing a filter having a pore size of less than 0.5 µm, preferably of less than 0.35 µm.

Instead of or in addition to a filter the delipidating device may comprise further components, in particular for centrifugation.

Advantageously, the device further comprises a pasteurizing unit for pasteurizing the delipidated milk. In an alternative embodiment, the pasteurizing unit may be arranged to pasteurize the human or animal milk prior to reducing the lipid content.

Preferably, the device further comprises a suction system and/or a pump system cooperating with the delipidating unit and/or the filtering unit to increase filtering efficiency and throughput. In order to provide the driving force for the filtering of the liquid in the first and/or in the second processing step, centrifugation may be employed.

In a preferred embodiment, the delipidating unit and the filtering unit are arranged in a closed system 61 where the delipidated milk is transferred from the delipidating unit to the filtering unit.

A reservoir may be provided in fluid connection with an output of the delipidating unit and with an input of the filtering unit. In this case, a volume of the reservoir is preferably 5 l or less, in particular 2.5 l or less.

In particular, a total volume of the protein-enriched fraction obtained from an initial volume of the human or animal milk is less than a fifth of the initial volume.

Both the delipidation step as well as the concentration step may be run under controlled temperature, e. g. in a controlled temperature environment. Different temperature regimes are possible. In a first regime, both steps are run at a temperature of 0-10° C. to avoid protein degradation and meet biosafety standards.

In a second regime, the temperature is selectively increased for certain substeps, in particular for the concentration step. Doing so increases the filtration process. After filtration, the products may be rapidly cooled.

Other advantageous embodiments and combinations of features come out from the detailed description below and the entirety of the claims.

BRIEF DESCRIPTION OF THE DRAWINGS

The drawings used to explain the embodiments show.

In the figures, the same components are given the same reference symbols.

PREFERRED EMBODIMENTS

Figure 1:
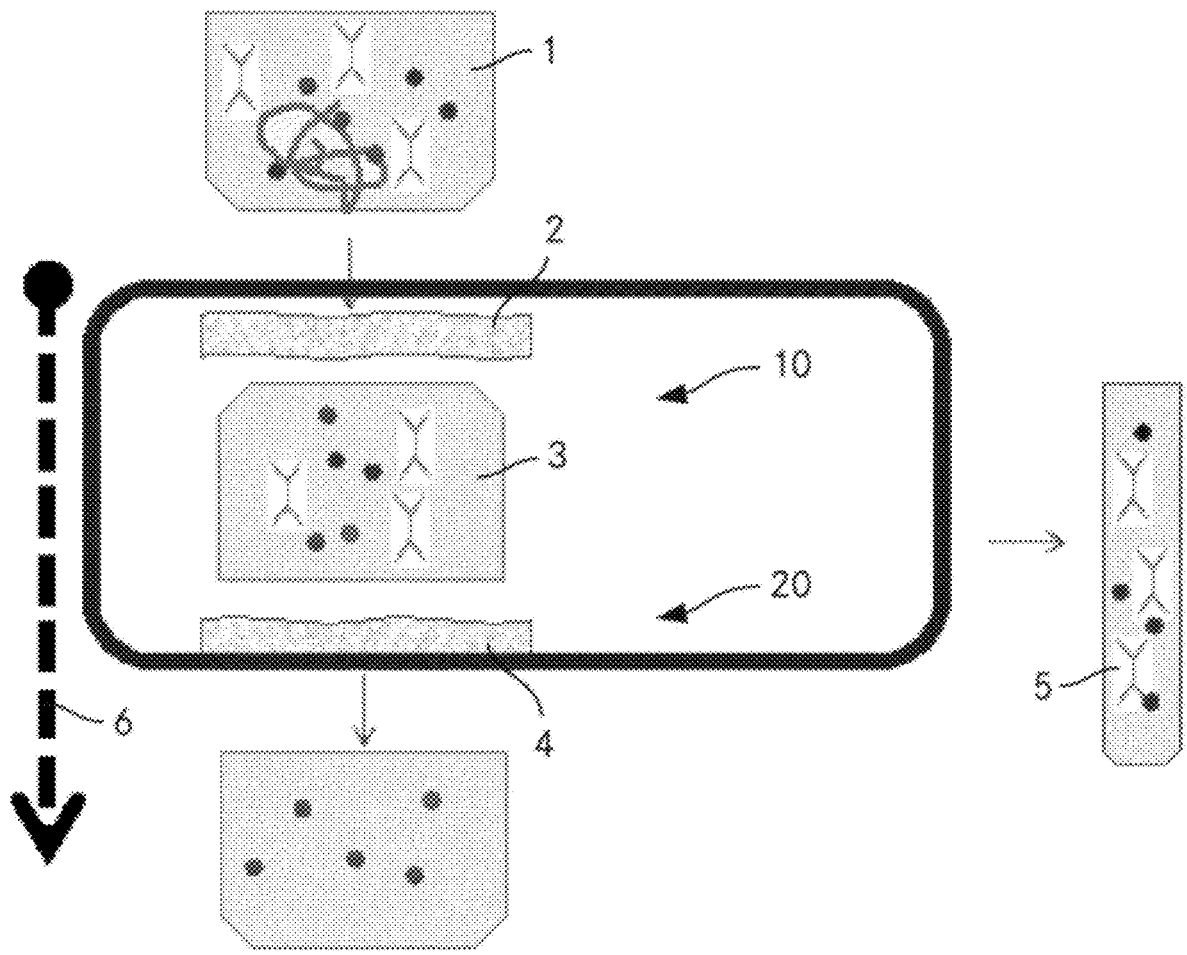
FIG. 1 A schematic illustration of an embodiment of the inventive method.

The FIG. 1 is a schematic illustration of an embodiment of the inventive method.

The starting product is human breast milk 1. It flows through a first filter 2 having a pore size of 0.2 μm (microfiltration step 10). The filter 2 is a 3-layer glass microfiber filter (GMF), available e. g. from GE Whatman. The filter 2 separates lipids from the rest of the human milk. Due to the small pore size, milk is also partially sterilized as most of the bacteria have a size of 0.5 μm or more. Nevertheless, it is advisable to pasteurize the starting product (or the intermediate product) due to bacteria with irregular shape, spores, etc.

Lipids precipitate on the first filter 2, the intermediate product (permeate) 3 is further treated by application of a second filter 4, having a nominal molecular weight limit of 10 kDa (nanofiltration step 20). Thereby, the concentration of proteins in the intermediate product 3 is increased. The result is a protein enriched fraction 5. Experiments have shown that the protein fraction does not precipitate and remains soluble.

The process is supported by a vacuum applied (as shown in more detail below, in connection with FIG. 2), as indicated by arrow 6. It can be further supported by air pressure. Instead, the driving force for squeezing the liquid through the first filter 2 and/or the second filter 4, centrifugation may be employed.

Both filters 2, 4 are single-usage. They are changed after each batch to avoid bacterial contamination.

The process is applied to batches of milk having a volume of 1.5 l (or less). The desired concentration factor is 10, i. e. the total volume of the protein-enriched fraction obtained from an initial volume of the human or animal milk is about a tenth of the initial volume. This yields a protein-enriched fraction with a protein amount of about 10 g/l.

Laboratory experiments have shown that the delipidation does not cause any significant loss of the total protein content since the filter has a very low unspecific binding capacity, i.e. proteins do not stick to the surface but freely pass the membrane.

Figure 2:
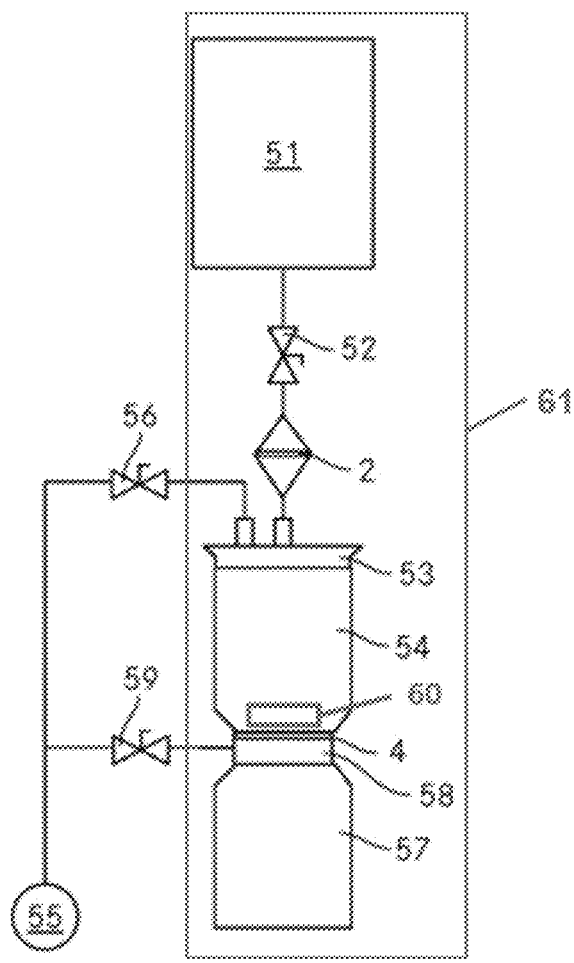
FIG. 2 a schematic view of an embodiment of the inventive device.

The FIG. 2 is a schematic view of an embodiment of the inventive device. The device comprises a first reservoir 51 with a volume of 1.5 l. It may be provided in the form of a bag. The reservoir is connected to the aforementioned replaceable first filter 2, where a valve 52 is arranged in the flow line between the first reservoir 51 and the first filter 2.

The output of the filter 2 is connected to a lid 53 of a second reservoir 54. A vacuum source 55 is also connected to the lid 53 in order to support the flow of the milk through the first filter 2, passing a valve 56. The second reservoir 54 has a volume of 0.5 l. It is connected to a third reservoir 57 with a volume of 0.5 l, the aforementioend second filter being arranged in the passage 58 between the second reservoir 54 and the third reservoir 57. A further connection connects the vacuum source 55 to the passage 58, passing another valve 59. This supports the extraction of the filtrate collected in the third reservoir 57 from the intermediate product stored in the second reservoir 54.

The invention is not limited to the embodiments described above. In particular, the inventive device may be supplemented with further elements to simplify the operation, in particular with respect to the supply and removal of educts and products. The vacuum system may be supplemented or replaced by an air pressure system and/or a pump system, e.g., based on a peristaltic pump. A stirring device 60, e.g., a magnetic stirrer, may be used to prevent accumulation of proteins on the surface of the membrane of the second filter.

Details of the components, such as filter materials and/or pore sizes, may be adapted.

The invention claimed is:

1. A vertically integrated device for on-site obtaining protein-enriched fractions from human or animal breast milk, comprising:
    a first reservoir having a volume of 1.5 L or less;
    a delipidating unit for reducing a lipid content in the human or animal breast milk to obtain delipidated milk, wherein the delipidating unit comprises a single-usage first filter, wherein the first reservoir is connected to the single-usage first filter, wherein a valve is arranged in a flow line between the first reservoir and the single-usage first filter;
    a second reservoir having a volume of 0.5 L, configured to receive an output of the single-usage first filter;
    an air pressure system, connected to the second reservoir in order to support a flow of the human or animal breast milk through the first filter passing a second valve;
    a third reservoir having a volume of 0.5 L, connected to the second reservoir;
    a filtering unit for increasing a protein concentration of the delipidated milk to obtain the protein-enriched fraction, comprising a single-usage second filter having a membrane and having a nominal molecular weight limit of 2 kDa or more, wherein the single-usage second filter is arranged in a passage between the second reservoir and the third reservoir, and wherein a further connection connects the air pressure system to the passage passing a third valve to support the extraction of filtrate collected in the third reservoir from an intermediate product stored in the second reservoir; and
    a stirring device configured to prevent accumulation of proteins on a surface of the membrane of the single-usage second filter;
    wherein
    (i) the delipidating unit and the filtering unit are vertically integrated; and
    (ii) the device is configured for on-site application.

2. The device of claim 1, wherein the single-usage first filter of the delipidating unit is a glass microfiber filter.

3. The device of claim 1, wherein the single-usage first filter of the delipidating unit has a pore size of less than 0.5 μm.

4. The device of claim 3, wherein the single-usage first filter of the delipidating unit has a pore size of less than 0.35 μm.

5. The device of claim 1, wherein the delipidating unit and the filtering unit are arranged in a closed system wherein the delipidated milk is transferred from the delipidating unit to the filtering unit.

6. The device of claim 1, wherein the single-usage second filter of the filtering unit has a nominal molecular weight limit of 5 kDa or more.

7. A device for obtaining protein-enriched fractions from human or animal breast milk, comprising:

a first reservoir having a volume of 1.5 L or less;
a delipidating unit comprising a single-usage first filter, wherein the first reservoir is connected to the single-usage first filter, wherein a first valve is arranged in a flow line between the first reservoir and the single-usage first filter;
a second reservoir having a volume of 0.5 L and comprising a lid configured to receive the output of the first filter, wherein the second reservoir further comprises a stirring device;
a vacuum source connected through a second valve to the lid of the second reservoir; and
a filtering unit comprising a single-usage second filter and a third reservoir, wherein
(i) the single-usage second filter is arranged in a passage between the second reservoir and the third reservoir,
(ii) the vacuum source is connected through a third valve to the passage; and
(iii) the third reservoir has a volume of 0.5 L;
wherein the delipidating unit, the second reservoir, the third reservoir, and the filtering unit are vertically integrated in a closed system; and
wherein the device is configured for on-site application.

8. The device of claim 7, wherein the single-usage first filter of the delipidating unit is a glass microfiber filter.

9. The device of claim 7, wherein the single-usage first filter of the delipidating unit has a pore size of less than 0.5 μm.

10. The device of claim 9, wherein the single-usage first filter of the delipidating unit has a pore size of less than 0.35 μm.

11. The device of claim 7, wherein the single-usage second filter of the filtering unit has a nominal molecular weight limit of 5 kDa or more.

* * * * *